United States Patent
Eisele et al.

(10) Patent No.: US 9,783,475 B2
(45) Date of Patent: Oct. 10, 2017

(54) METHOD FOR FORMING CYCLOHEXANONE FROM CYCLOHEXANOL

(71) Applicant: BASF SE, Ludwigshafen (DE)

(72) Inventors: Dennis Eisele, Lake Jackson, TX (US); Bita Fillipi, Pearland, TX (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/227,255

(22) Filed: Aug. 3, 2016

(65) Prior Publication Data
US 2017/0050911 A1    Feb. 23, 2017

Related U.S. Application Data

(60) Provisional application No. 62/207,607, filed on Aug. 20, 2015.

(51) Int. Cl.
*C07C 45/00* (2006.01)

(52) U.S. Cl.
CPC ........ *C07C 45/002* (2013.01); *C07C 2601/14* (2017.05)

(58) Field of Classification Search
CPC .................................................. C07C 45/002
USPC ........................................................ 568/361
See application file for complete search history.

(56) References Cited

U.S. PATENT DOCUMENTS 4,310,703 A * 1/1982 Tamaru ................. B01J 23/868
                                                              568/361
4,918,239 A * 4/1990 Wang ....................... B01J 23/80
                                                              568/360

OTHER PUBLICATIONS

Dake, S.B., Varshney, A.K., "New Trends in Dehydrogenation of Cyclohexanol to Cyclohexanone", Research Centre, 750, India, pp. 373-378.
Musser, M. "Cyclohexanol and Cycloheanone",Ullman's Encyclopedia of Industrial Chemistry, (2012), pp. 49-60.
Cubberley, A., Mueller, M., "Equilibrium Studies on the Dehydrogenation of Primary and Secondary Alcohols. II. Cyclohexanols" The Barrett Division research Labatory, (1947), pp. 1535-1536.

* cited by examiner

*Primary Examiner* — Sikarl Witherspoon
(74) *Attorney, Agent, or Firm* — Christy Spradley

(57) ABSTRACT

A method for forming cyclohexanone from cyclohexanol is provided in which two or more cyclohexanol dehydrogenation reactors and associated condensers are operably connected in series so as to increase relative concentration of cyclohexanone in the formed product through the use of Le Châtelier's principle.

18 Claims, 9 Drawing Sheets

METHOD FOR FORMING CYCLOHEXANONE FROM CYCLOHEXANOL

This patent application claims the benefit of U.S. provisional patent application Ser. No. 62/207,607 filed Aug. 20, 2015, incorporated in its entirety herein by reference.

BACKGROUND OF THE INVENTION

1. Field of the Invention

The subject invention generally relates a method for forming cyclohexanone, and more particularly to a method for forming cyclohexanone from cyclohexanol.

2. Description of the Related Art

The production of cyclohexanone from a dehydrogenation reaction of cyclohexanol in the presence of a catalyst is known. Conventional large scale production of cyclohexanone typically utilizes a system including a single dehydrogenation reactor coupled to a distillation unit. In these conventional systems, cyclohexanol is fed into the single dehydrogenation reactor, where it is vaporized and dehydrogenated to cyclohexanone and hydrogen gas in the presence of a catalyst. The resultant product formed by this method includes large amounts of unreacted cyclohexanol that is separated from the formed cyclohexanone in the distillation unit, and the separated highly concentrated cyclohexanol recovered after distillation from the distillation unit may then be fed back into the single dehydrogenation reactor for further processing.

SUMMARY OF THE INVENTION AND ADVANTAGES

The subject application refers to a method for producing cyclohexanone from cyclohexanol in which two or more cyclohexanol dehydrogenation reactors and condensers are operably connected in series, with hydrogen gas formed as a product removed between dehydrogenation steps, so as to increase relative concentration of cyclohexanone in the formed product of the method.

The method comprises: introducing liquid cyclohexanol into a first cyclohexanol dehydrogenation reactor; vaporizing the liquid cyclohexanol within the first cyclohexanol dehydrogenation reactor to form vaporized cyclohexanol; dehydrogenating the vaporized cyclohexanol in the presence of a dehydrogenation catalyst to form vaporized cyclohexanone and hydrogen gas; condensing the formed vaporized cyclohexanone and any remaining vaporized cyclohexanol within a first condenser to form liquid cyclohexanone and liquid cyclohexanol; removing the formed hydrogen gas; vaporizing the formed liquid cyclohexanone and liquid cyclohexanol within a second cyclohexanol dehydrogenation reactor to form vaporized cyclohexanone and vaporized cyclohexanol; dehydrogenating the vaporized cyclohexanol from the second cyclohexanol dehydrogenation reactor in the presence of a dehydrogenation catalyst to form additional vaporized cyclohexanone and additional hydrogen gas; and condensing the formed vaporized cyclohexanone and any remaining vaporized cyclohexanol within a second condenser to form liquid cyclohexanone and liquid cyclohexanol as a product.

The use of two or more cyclohexanol dehydrogenation reactors and condensers operably coupled in series as in the present invention, wherein hydrogen gas produced in a dehydrogenation step within a respective cyclohexanol dehydrogenation reactor is removed prior to subsequent dehydrogenation reactions of any remaining cyclohexanol occurring in the next cyclohexanol dehydrogenation reactor, allows further dehydrogenation of any remaining cyclohexanol to take place in accordance with Le Châtelier's principle and without the need for distillation of the formed cyclohexanone from the remaining cyclohexanol prior to any subsequent dehydrogenation step. The resultant product resulting after each dehydrogenation reaction has an increased concentration of cyclohexanone relative to cyclohexanol in the immediately prior dehydrogenation reactor in series.

Still further, by reducing the concentration of unreacted cyclohexanol in the resultant product, the amount of cyclohexanol that needs to be separated from the formed cyclohexanone and recycled (i.e., reintroduced to another dehydrogenation reactor after recovery from distillation to form additional cyclohexanone) is correspondingly reduced.

BRIEF DESCRIPTION OF THE DRAWINGS

Other advantages of the present invention will be readily appreciated, as the same becomes better understood by reference to the following detailed description, when considered in connection with the accompanying drawing.

DETAILED DESCRIPTION OF THE INVENTION

As noted above, the subject application refers to a method for producing cyclohexanone from cyclohexanol in which two or more cyclohexanol dehydrogenation reactors and condensers are operably connected in series so as to increase relative concentration of cyclohexanone in the formed product of the method as compared with traditional cyclohexanone method that utilize a single dehydrogenation reactor coupled to a distillation unit to form the cyclohexanone.

Figure 1:
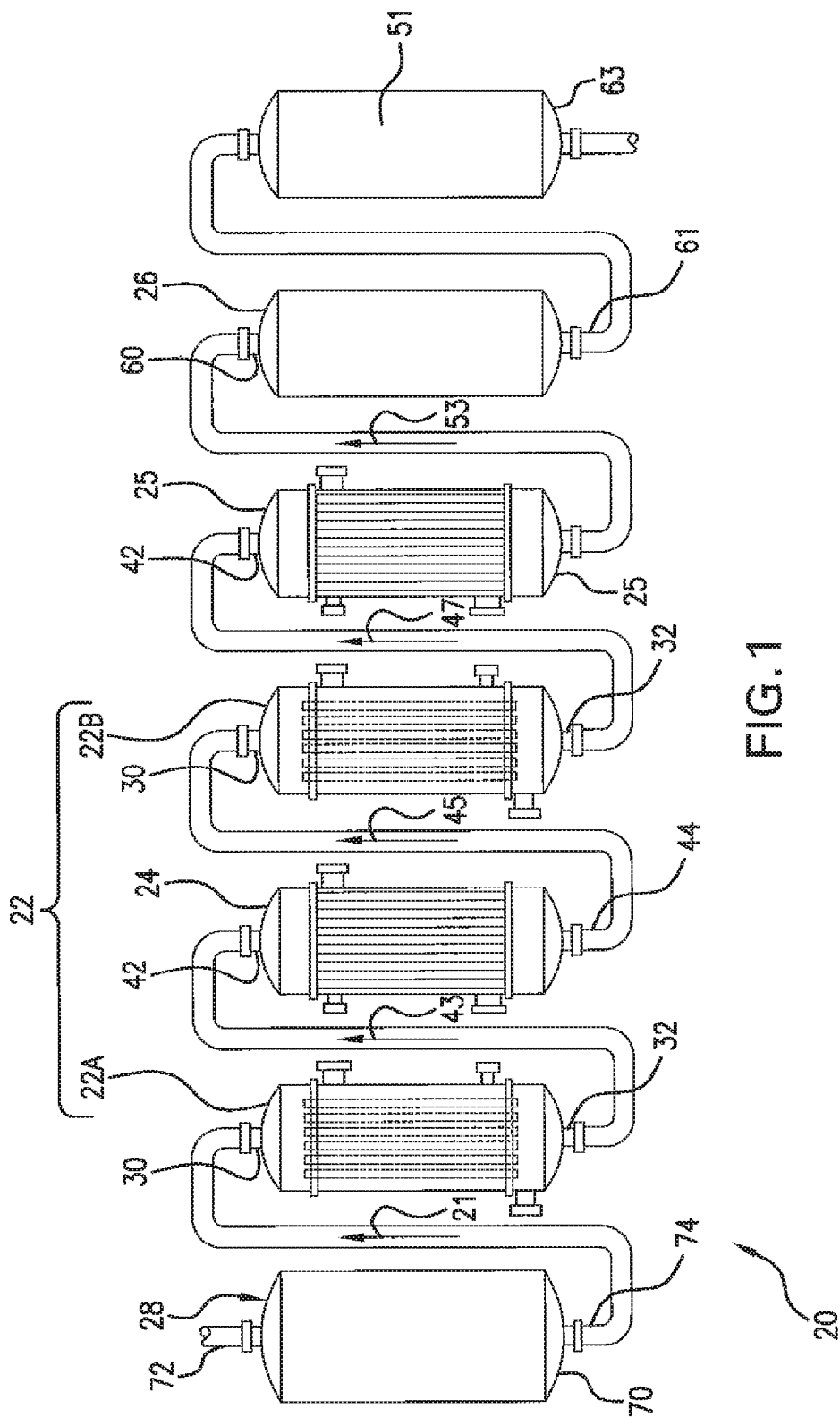
FIG. 1 is a perspective view of a cyclohexanone production system in accordance with one embodiment of the present invention.

Referring first to FIG. 1, a cyclohexanone production system 20 in accordance with one embodiment of the present invention includes, as its major components, a series of cyclohexanol dehydrogenation reactors 22 (here shown as two cyclohexanol dehydrogenation reactors 22A and 22B), a condenser 24 operatively coupled between each respective adjacent pair of the cyclohexanol dehydrogenation reactors 22, a last condenser 25 operatively coupled to the last one 22B of the series of cyclohexanol dehydrogenation reactors 22, and a distillation unit 26 operatively coupled to the last in the series of condensers (here shown as a second condenser 25). In addition, the production system 20 includes a cyclohexanol unit 28 that is operatively coupled to the first one 22A of the series of cyclohexanol dehydrogenation reactors 22.

In general, the method of the present invention therefore includes introducing cyclohexanol from the cyclohexanol unit 28 as a part of a fluid stream 21 and into the series of cyclohexanol dehydrogenation reactors 22, 22A, 22B and condensers 24, 25. Within these reactors 22, 22A, 22B and condensers 24, 25, the cyclohexanol is dehydrogenated to form cyclohexanone. The formed cyclohexanone and any residual cyclohexanol and other hydrocarbon products are removed from the last condenser 25 and are introduced to the distillation unit 26, wherein the cyclohexanone is separated from any residual cyclohexanol and other hydrocarbon products to produce a high purity cyclohexanone that can be removed from the distillation unit 26 and stored in a container 63. This general method will be described in further detail in the logic flow diagram of FIG. 8 below.

Figure 2:
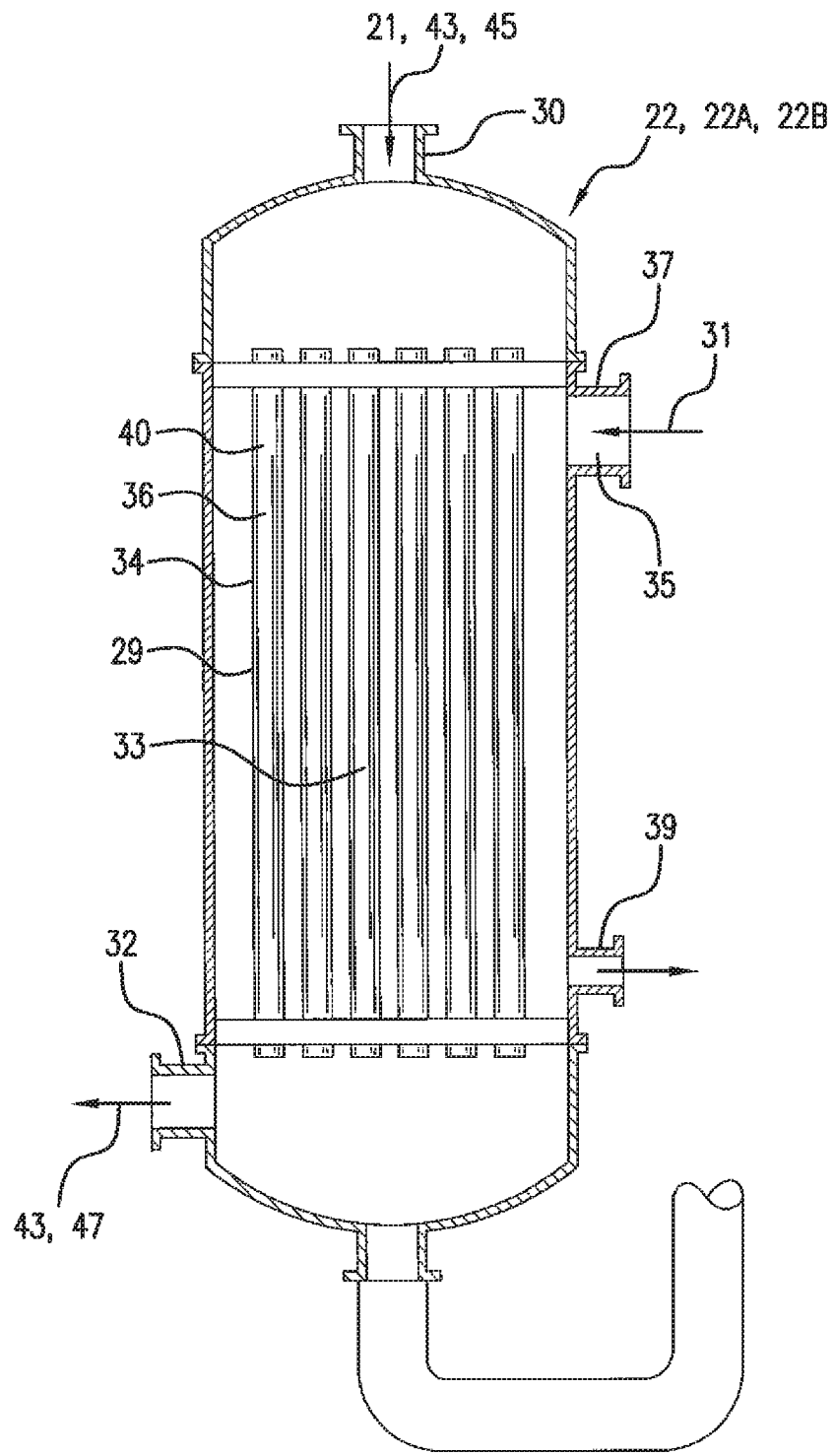
FIG. 2 is a cross-sectional view of a cyclohexanol dehydrogenation reactor of FIG. 1.

As best shown in FIG. 2, each respective one of the cyclohexanol dehydrogenation reactors 22, 22A, and 22B includes an inlet 30 and an outlet 32 and defines an interior region 33 between the inlet 30 and outlet 32. Contained between the inlet 30 and outlet 32 and within the interior region 33 is a catalyst bed 34 that includes a dehydrogenation catalyst 36.

In the embodiment shown in FIG. 2, the catalyst bed 34 includes a series of tubes 29 filled with a dehydrogenation catalyst 36. Each cyclohexanol dehydrogenation reactor 22, 22A, 22B also includes a heating element, shown as a hollow tube 37 in FIG. 2, that is capable of heating the interior region 33 of the reactor 22 to temperatures sufficient to vaporize the fluid components contained within the interior region 33.

As also shown in FIG. 2, the hollow tube 37 runs through the interior region 33 of the reactor 22 and includes an inlet 35 and an outlet 39. A combustion gas 31 heated to a temperature greater than the vaporization temperature of cyclohexanol and cyclohexanone is introduced through the inlet 35 and exits through the outlet 39 of the hollow tube 37. Convection heat from the hollow tube 37 flows from the heated combustion gas 31 flowing through the interior region 40 of the hollow tube 37 and into the interior of region 33 of reactor 22. This convection heat heats the fluid stream 21, 43, 45 of cyclohexanol and introduced through the inlet 30 and within the interior region 33 of the reactor 22, 22A, 22B (but not within the hollow tube 37) above their respective vaporization temperatures, as will be discussed further below.

The dehydrogenation catalysts 36 are those conventionally employed in dehydrogenation methods, for example the heavy metals of the $5^{th}$ to $8^{th}$ groups and/or of the $1^{st}$ group of the periodic system, as well as their oxides and sulfides. Suitable metals are nickel, cobalt, and noble metals, such as platinum, palladium, rhodium and iridium. In certain embodiments, the metal is zinc. The dehydrogenation catalysts 36 can be used as such or after application to a carrier 38, for example calcium oxide, pumice, silica, bleaching earths, synthetic silicates, active aluminas or bauxite in the form of pills, granulated or powder form. In certain embodiments, the dehydrogenation catalysts 36 are used with contents of 3 to 60 percent by weight, such as 5 to 15 percent by weight, of active components, e.g. zinc.

Figure 3:
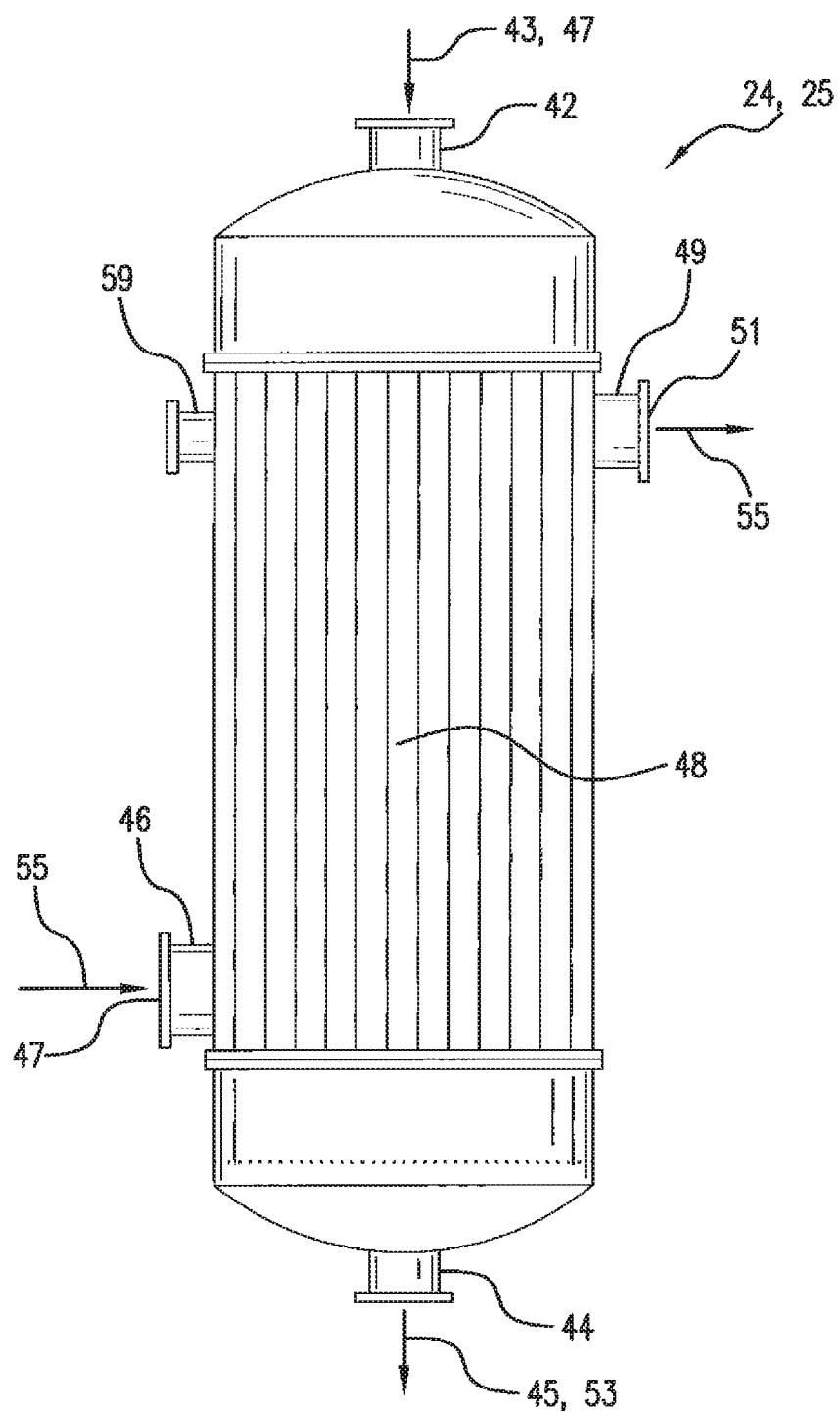
FIG. 3 is a cross-sectional view of a condenser of FIG. 1.
Figure 4:
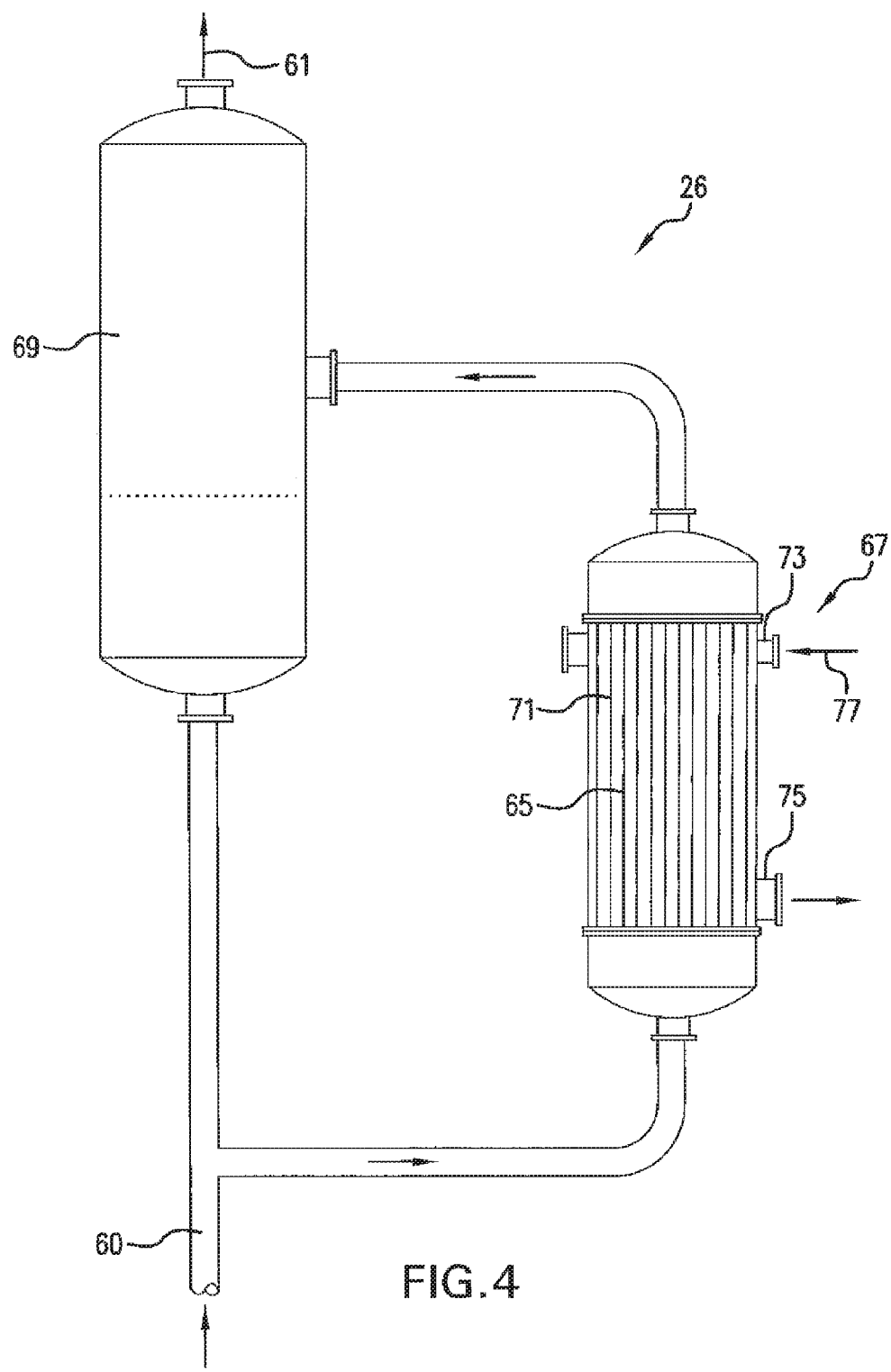
FIG. 4 is a cross-sectional view of the distillation unit of FIG. 1.

Referring now to FIG. 3, each of the condensers 24, 25 in accordance with one embodiment of the present invention, includes an inlet 42 that is fluidically coupled to the outlet 32 of the adjacent cyclohexanol dehydrogenation reactor 22, 22A, 22B. The condenser 24, 25 also includes an outlet 44 that is fluidically coupled to the inlet 30 of the next adjacent cyclohexanol dehydrogenation reactor 22, 22B or to the inlet 60 of the distillation unit 26, as shown in FIG. 4. The condenser 24, 25 further includes a hydrogen gas vent 59. The condenser 24, 25 also includes one or more cooling elements, here shown as a hollow tube 49, contained within the interior region 48 of the condenser 24, 25 that are designed to reduce the temperature within the interior region 48 to a temperature below the condensation temperature of vaporized cyclohexanol and cyclohexanone introduced to the condenser 24, 25 through its inlet 42 as a vapor stream 43, 47 as will be described in further detail below.

The hollow tube 49 allows for the flow of a cooling fluid or gas 55 therethrough, with the cooling fluid or gas 55 coupled to a fluid source not shown) entering the tube 46 at its inlet 47 and exiting the tube 49 at an outlet 51 remote from the inlet 47. The outer surface of the hollow tube 49 provides a cooling surface that is used to condense the vaporized cyclohexanol and cyclohexanone introduced into the interior region 48 to liquid form. The hollow tube 49 may be connected in series to the hollow tube 37 of the reactors 22, such that the cooling fluid or gas 55 and the combustion gas 31 are the same gas, and thus the collection of hollow tubes 37 and 49 of the coupled reactors 22, 22A, 22B and condensers 24, 25 may form a heat exchanger. Alternatively, such as shown in FIG. 3, the cooling fluid or gas 55 is distinct and separate from the combustion gas 31 of FIG. 2.

The distillation unit 26 may be a single unit or a series of distillation units, but is shown in FIGS. 1 and 4 as a single distillation unit 26 for illustrative purposes.

Referring to FIG. 4, each distillation unit 26 includes an inlet 60 fluidically coupled to the outlet 32 of the last one of the series of cyclohexanol dehydrogenation reactors 22, 22B. The distillation unit 26 also includes a vapor outlet 61 for stepwise remove of the pure distillates (including the purified cyclohexanone), which may then be stored in a plurality of storage containers (shown as 63 in FIG. 1). The distillation unit includes a heater region 67 that boils the liquid contained in its interior region 65 and allows the vaporized component to be drawn off through the vapor outlet 61 to a collection tank (not shown), whereas the remaining distillate that does not exit through the vapor outlet 61 is condensed into a holding unit 69 and recycled into the heater region 67.

The heater region 67 includes a series of one or more hollow tubes 71 that extend within the interior region 65 and are coupled to a fluid inlet 73 and a fluid outlet 75. Pressurized steam 77 enters the series of hollow tubes 71 through the fluid inlet 73, and the cooled condensate 75 exits the hollow tubes 71 through the fluid outlet 75. Typically, the pressurized steam has a pressure ranging from 3240 to 3310 kPa (kilopascals), such as approximately 3275 kPa (approximately 475 psi). Heat radiates through the hollow tubes 71 and into the interior region 65. The steam 77 entering through the fluid inlet 73 may be the same fluid 31 utilized in the reactors 22 and condensers 24, or may be directed to the distillation unit 26 from an alternative source.

Similar to above, in certain embodiments, the series of hollow tubes 71 may be connected in series to each of the hollow tubes 37 of the reactors 22, 22A, 22B such that the combustion gas 31 and the pressurized steam 77 are the same gas. Similarly, the hollow tubes 71 may be connected in series to the hollow tubes 46 of the condensers 24, 25 to form a heat exchanger, and as such the pressurized steam 77 may be cooled and form the cooling gas 47. Still further, all of the hollow tubes 37, 46 and 71 may be connected in series to form a heat exchanger in yet another embodiment, wherein the combustion gas 31, the cooling fluid 47, and the steam 77 are the same fluid component.

The cyclohexanol unit 28, as shown in FIG. 1, includes a feed storage tank 70 having an inlet 72 for receiving a cyclohexanol in liquid form and an outlet 74 fluidically coupled to the inlet 30 of the first cyclohexanol dehydrogenation reactor (referred to by both reference numbers 22 and 22A).

Figure 5:
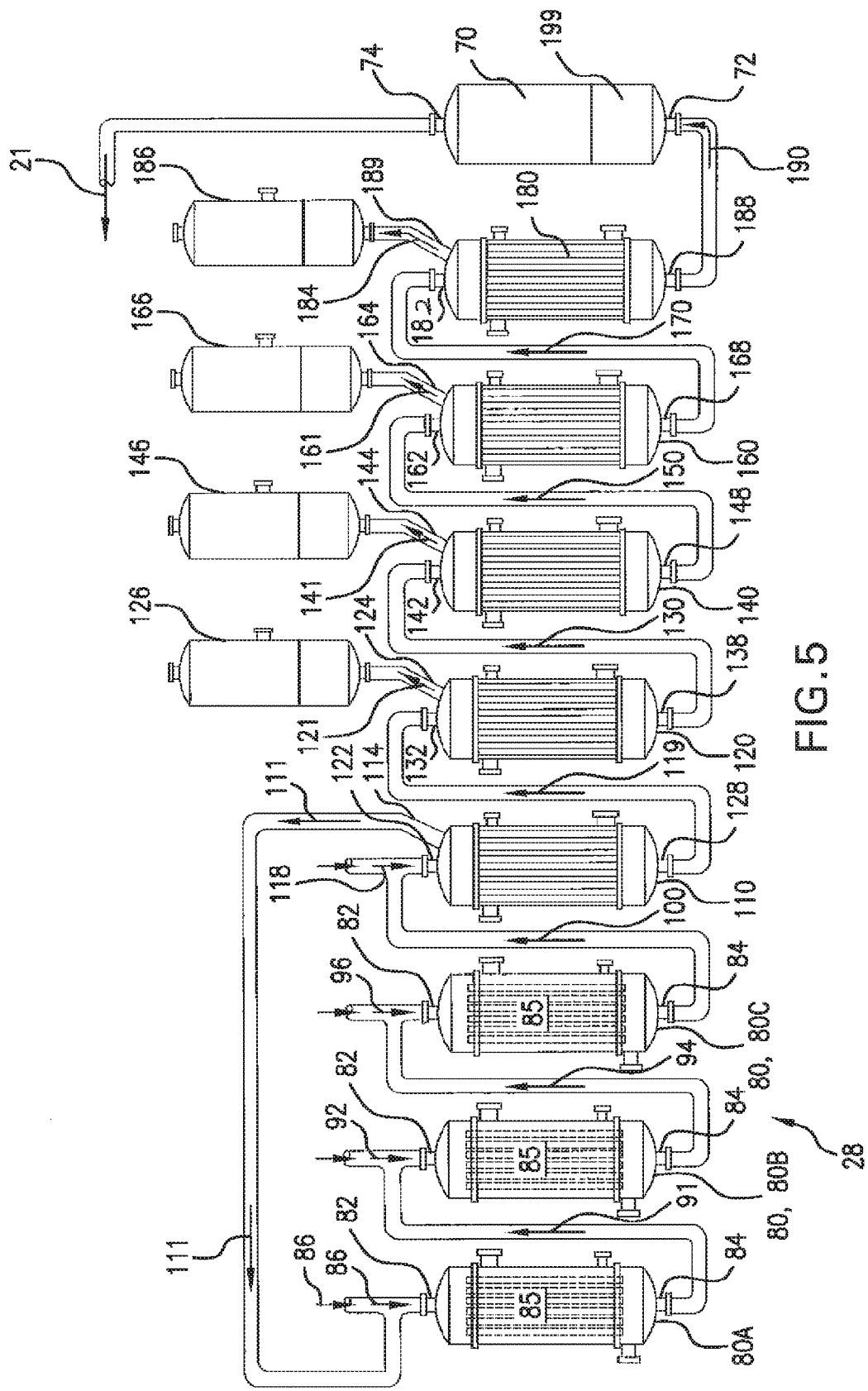
FIG. 5 is a perspective view of a cyclohexanol production system of FIG. 1 including a series of cyclohexanol reactors and a series of distillation units in accordance with one embodiment of the present invention.
Figure 6:
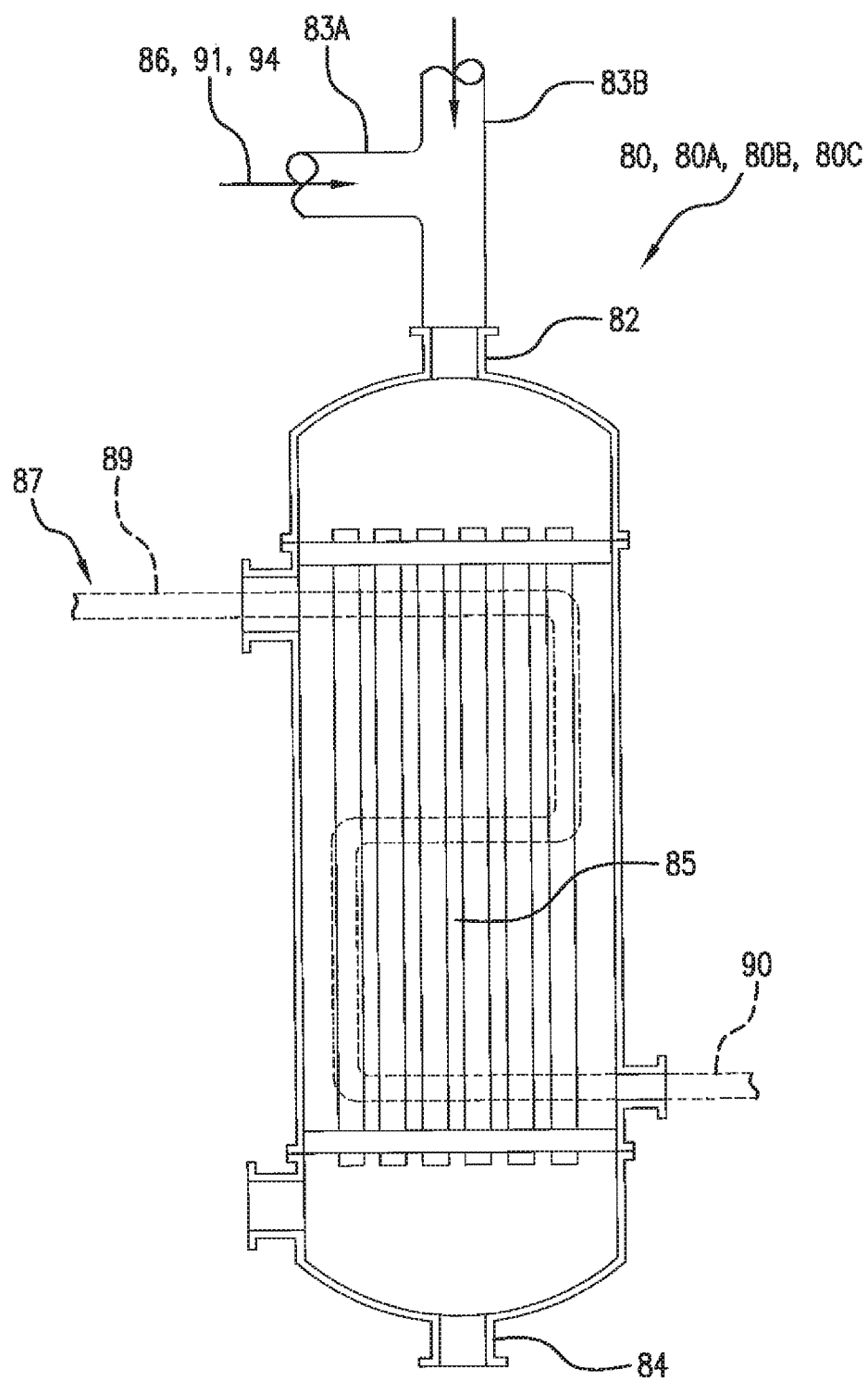
FIG. 6 is a cross-sectional view a cyclohexanol reactor of FIG. 5.
Figure 7:
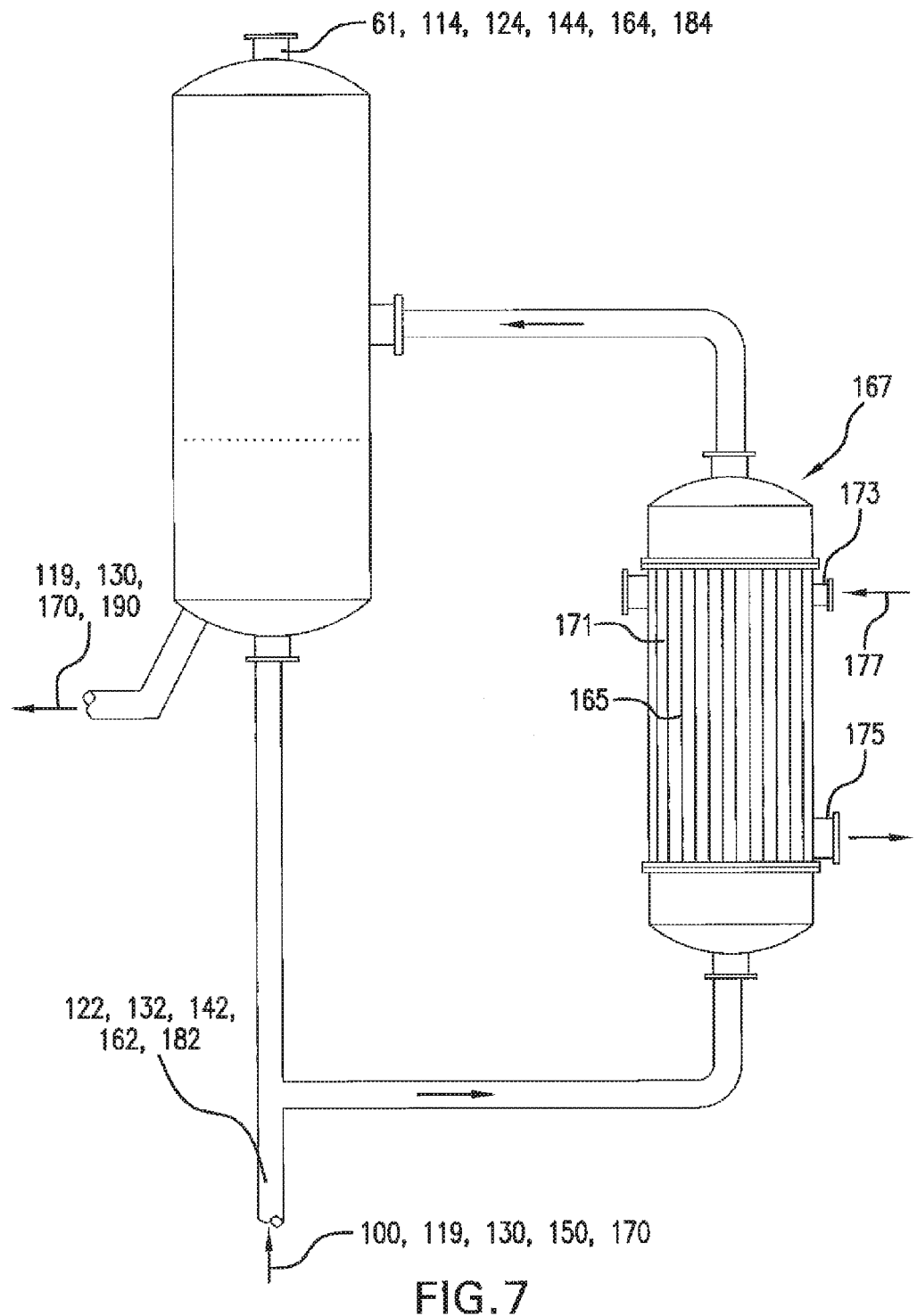
FIG. 7 is a cross-sectional view of a distillation unit of FIG. 5.

Still further, as also shown in FIGS. 5-7, the cyclohexanol unit 28 may optionally be configured to form cyclohexanol from cyclohexane and include a series of reactors 80, 80A, 80B, 80C that are connected in series to a series of distillation units 110, 120, 140, 160 and 180, the last 180 of which is fluidically coupled to the feed storage tank 70.

Referring to FIG. 6, each of the reactors 80, 80A, 80B, 80C include an inlet 82 and an outlet 84 and define an interior region 85 between the inlet 82 and the outlet 84. The inlet 82 may include a first portal 83A and one or more additional portals 83B that funnel together at the inlet 82. The first portal 83A is used to introduce the cyclohexane fluid stream 86 into the first reactor 80A, and is used to introduce the cyclohexanol fluid stream 91, 94 from subsequent fluid reactors 80B or 80C. The additional portals 83B are typically included on the reactors 80A, 80B, 80C in the series for the introduction of air and additional catalyst material to be combined with the respective fluid streams 86, 91, 94, as will be described further below.

The reactors 80, 80A, 80B, 80C also include a cooling device for cooling the interior region 85 to the desired temperature since the reaction of cyclohexane to cyclohexanol is exothermic. Typically, the cooling device is an annular space around the tubes 87 having an inlet 89 and an outlet 90. Liquid recycled from the recovery part of the distillation unit 26 enters the hollow tube 87 through the inlet 89 and exits through the outlet 90 and aids in converting the cyclohexane to cyclohexanol, as will be described further below.

The distillation units 110, 120, 140, 160 and 180, as shown in FIG. 7, are of the same basic design as the distillation unit 26 of FIG. 4 and each include a respective inlet 122, 132, 142, 162, 182 and outlet 128, 138, 148, 168, 188, as shown in FIG. 5, as well as a vapor outlet, or vent 114, 124, 144, 164, 184 for the removal of vaporized distillates. The distillation units 110, 120, 140, 160 and 180 also each include the heater region that boils the liquid contained in its interior region and allows the vaporized component to be drawn off through the vapor outlet, whereas the remaining distillate that does not exit through the vapor outlet but is condensed into the holding unit (not shown) and recycled into the heater region 167.

Still further, the heater region 167 includes a series of one or more hollow tubes 171 that extend within the interior region 165 and are coupled to the fluid inlet 173 and the fluid outlet 175. Pressurized steam 177 enters the series of hollow tubes 171 through the fluid inlet 173, and the condensate exits the hollow tubes 171 through the fluid outlet 175. Typically, the pressurized steam 177 has a pressure ranging from 3240 to 3310 kPa (kilopascals), such as approximately 3275 kPa (approximately 475 psi). Heat radiates (flows) through the hollow tubes 171 and into the interior region 165. The steam 177 entering through the fluid inlet 173 of each of the distillation units 110, 120, 140, 160 and 180 may be the same fluid, and may be the same fluid 31 utilized in the distillation unit 26, the reactors 22 and/or the condensers 24, 25 or may be directed to one or more of the distillation units 110, 120, 140, 160 and 180 from an alternative source.

Within these distillation units 110, 120, 140, 160 and 180, the vapor exiting through the vent 114, 124, 144, 164, 184 may be collected and stored in a container unit (shown in FIG. 5 by reference numbers 126, 146, 166 and 186) or alternatively may be recycled to the first dehydrogenation reactor 22A, as will be described in the methods below.

The method of the present invention that utilizes the cyclohexanone processing unit 20 of FIGS. 1-7 to produce high purity cyclohexanone is illustrated in the logic flow diagram of FIG. 8 in accordance with one embodiment of the present invention as follows. In the embodiment described in the logic flow diagram of FIG. 8, two dehydrogenation reactors 22A, 22B are connected in series between a cyclohexanol unit 28 and a distillation unit 26, although in other embodiments of the present invention the number of dehydrogenation reactors, and the relative configuration of the cyclohexanol unit 28 and distillation unit 26, may be altered from the description below.

Figure 8A:
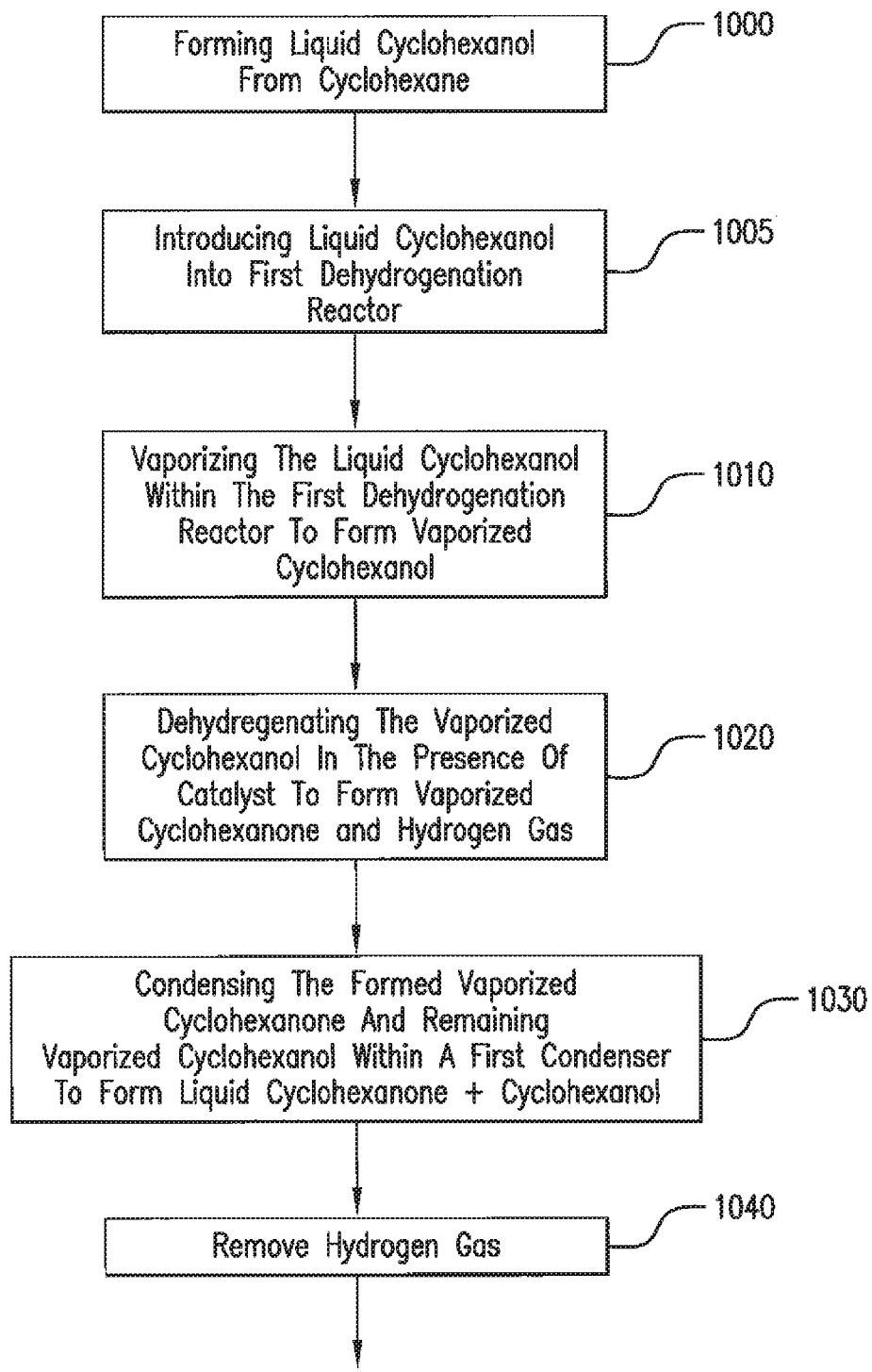
FIGS. 8A and 8B are logic flow diagrams for forming cyclohexanone in the cyclohexanone production system of FIGS. 1-7 in accordance with one embodiment of the present invention.
Figure 8B:
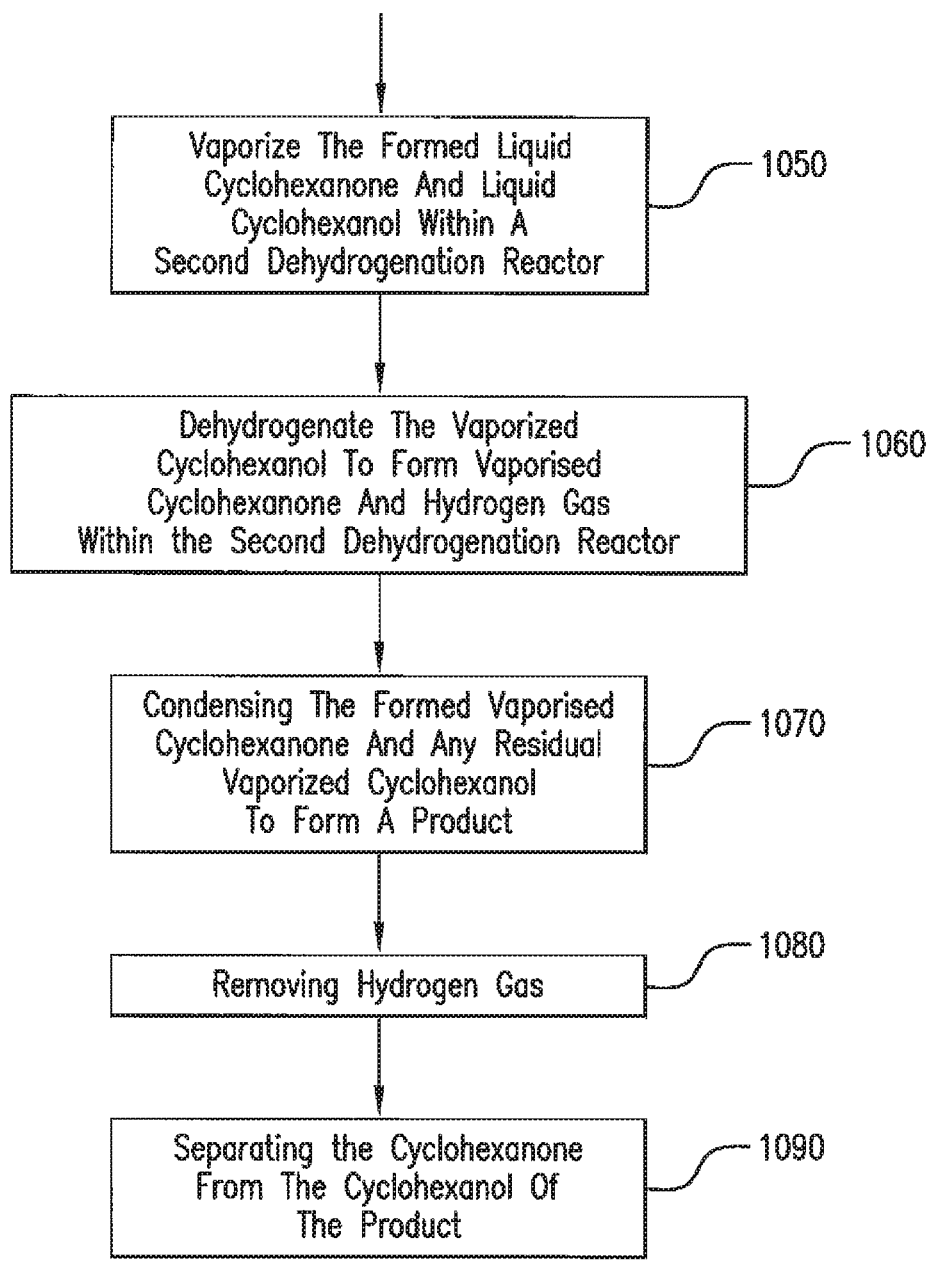

Referring first to Step 1005 of FIG. 8, the method of the present invention begins by introducing liquid cyclohexanol into the first cyclohexanol dehydrogenation reactor 22A.

In certain embodiments, wherein the cyclohexanol is housed in the storage tank 70 of the cyclohexanol unit 26 as in FIG. 1 or FIG. 5 above, Step 1005 is accomplished by removing the liquid cyclohexanol (product 199 as shown in FIG. 5) from the outlet 74 of the storage tank 70 as a fluid stream 21 and then introducing the fluid stream 21 through the inlet 30 of the first cyclohexanol dehydrogenation reactor 22.

The cyclohexanol introduced in Step 1005 as a fluid stream 21 from the storage tank 70 is generally not pure cyclohexanol, in that it may include residual amounts of other hydrocarbons, including for example cyclohexanone (see, for example, the method of Step 1000 below, wherein the product formed and stored in the storage tank 70 may include both cyclohexanol and cyclohexanone). Hence, any reference to the fluid stream 21 and to cyclohexanol contained within the fluid stream 21 is not meant to infer that the fluid stream 21, or the corresponding product 199, is pure cyclohexanol, but may and typically does include residual amounts of other hydrocarbons such as cyclohexanone.

As a precursor to Step 1005, in certain alternative and related methods of the present invention, the liquid cyclohexanol introduced in Step 1005 is first formed from cyclohexane in the cyclohexanol unit 28 in Step 1000. Alternatively, the starting material may be cyclohexanol.

In Step 1000, the step of forming liquid cyclohexanol from cyclohexane, in accordance with an alternative method of the present invention and as illustrated in FIG. 5, begins wherein cyclohexane, air, and a catalytic oxidation catalyst (typically a cobalt catalyst mixed with cyclohexanone) are combined and introduced through the inlet 82 of the first reactor 80A and into the interior region 85 as a fluid stream 86. The interior region 85 of the reactor 80A is cooled by the cooling tube 87, as the formation of cyclohexanol from cyclohexane is an exothermic reaction. The reaction product, including the produced cyclohexanol and any remaining unreacted cyclohexane, is removed from the interior region 85 of the first reactor 80A through the outlet 84 as a fluid stream 91.

The fluid stream 91 is then combined with a supplemental amount of air and a supplemental amount of catalytic oxidation catalyst (typically again a cobalt catalyst mixed with cyclohexane), and the newly combined fluid stream 92 is introduced through the inlet 82 of the second reactor 80B. Similar to the first reactor 80A, the interior region 85 of the second reactor 80B is cooled by the cooling tube 87. Again, similar to the first reactor 80A, the reaction product, including the produced cyclohexanol and any remaining unreacted cyclohexane, is removed from the second reactor 80B through the outlet 84 as a fluid stream 94.

The fluid stream 94 is then combined with yet another supplemental of air and yet another supplemental amount of catalytic oxidation catalyst (typically again a cobalt catalyst mixed with cyclohexane), and the combined stream 96 is introduced through the inlet 82 next adjacent reactor 80, here shown as the last reactor SOC. Similar to the first reactor 80A, the interior region 85 of the last reactor 80C is cooled by the cooling tube 87. Again, similar to the first reactor 80A and second reactor 80B, the reaction product, including the produced cyclohexanol and any remaining unreacted cyclohexane, is removed from last reactor 80C through the outlet 84 as a fluid stream 100.

It should be appreciated by those of ordinary skill that the composition of the fluid stream exiting each adjacent reactor 80A, 80B and 80C increases in concentration of cyclohexanol relative to cyclohexane.

While the logic flow diagram of FIG. 8 describes Step 1000 as including three separate reactors 80A, 80B and 80C to coincide with the illustration in FIG. 5, Step 1000 could include additional reactors 80 located in series between the first 80A and last reactor 80C that are not illustrated or described with respect to FIG. 5.

The reaction stream 100 exiting the last reactor 80C is then introduced through a series of distillation units 110, 120, 140, 160, 180, wherein the cyclohexanol from the fluid stream 100 is separated from the cobalt catalyst and cyclohexanone, and lower boiling point and higher boiling point hydrocarbon products produced, through distillation, as described below.

Prior to the first distillation unit 110, the fluid stream 100 is combined with air and catalyst to form a fluid stream 118 that enters the first distillation unit 100 through its inlet 122.

Within the first distillation unit 110, the stream 118 is heated to a temperature sufficient to vaporize the remaining cyclohexane, which is then vented as a fluid stream 111 from the first distillation unit 110 through a vent 114 and recycled to the first reactor 80A, wherein it is combined with additional cyclohexane at the fluid inlet 82. The catalytic oxidation catalyst may also be separated from the vaporized cyclohexane in this reactor.

The remaining distillate within the first distillation unit 110, which is a combination of cyclohexanol and cyclohexanone, exits the first distillation unit 110 through its outlet 128 as a fluid stream 119 and is introduced through an inlet 132 of a second distillation unit 120.

The fluid stream 119 is heated within the second distillation unit 120 to a temperature less than the vaporization temperature of the cyclohexanol and cyclohexanone but above the vaporization temperature of other hydrocarbons. In certain embodiments, the fluid stream 119 is heated to a temperature from 151 to 161° C. at an absolute vacuum pressure ranging from 931 to 971 kPa, such as 155° C. at 951 kPa. These vaporized hydrocarbons 121 are vented from the second distillation unit 120 through a vent 124 and captured in a storage tank 126. The remaining liquid cyclohexanol and cyclohexanone is removed from the second distillation unit 120 through its outlet 138 as a fluid stream 130.

The fluid stream 130 is introduced within the inlet 142 of a third distillation unit 140. Within the third distillation unit 140, the fluid stream 130 is heated to a temperature above the vaporization temperature of cyclohexanone but below the vaporization temperature of cyclohexanol. The vaporized cyclohexanone 141 is then vented out of the third distillation unit 140 through a vent 144 and captured in a storage tank 146. The remaining fluid stream, which includes cyclohexanol and residual cyclohexanone, is removed from the third distillation unit 140 through an outlet 148 as a fluid stream 150.

The fluid stream 150 is introduced within the inlet 162 of a fourth distillation unit 160. Within the fourth distillation unit 160, the fluid stream 150 is again heated to a temperature above the vaporization temperature of cyclohexanone but below the vaporization temperature of cyclohexanol, such as from 72 to 92° C. at an absolute vacuum pressure ranging from 275 to 345 kPa, such as 82° C. at 310 kPa. The vaporized cyclohexanone is then vented out of the fourth distillation unit 160 as a fluid stream 161 through a vent 164 and captured in the storage tank 166 or in an additional separate storage tank (not shown). The remaining fluid stream, which includes cyclohexanol and residual cyclohexanone, is removed from the fourth distillation unit 160 through an outlet 168 as a fluid stream 170.

The distillation steps described as a portion of Step 1000 of FIG. 8 may be repeated with additional distillation units (not shown) to further remove the cyclohexanone that may be captured into further storage tanks, and thus with each successive distillation the fluid stream remaining includes a higher concentration of cyclohexanol relative to cyclohexanone.

The fluid stream 170 is then introduced through an inlet 182 into a final distillation unit 180. In the final distillation unit 180, the fluid stream 170 is heated to a temperature above the vaporization temperature of cyclohexanol, such as from 84 to 104° C. at an absolute vacuum pressure ranging from 551 to 621 kPa, such as 94° C. at 586 kPa. The vaporized cyclohexanol is vented from the final distillation unit 180 as a fluid stream 181 through a vent 189, wherein it is captured in a storage tank 186.

The remaining cyclohexanone and any residual cyclohexanol exits the last distillation unit 180 through its outlet 188, which is fluidically connected to the inlet 72 of the feed storage tank 70.

The resultant product 190 provided to the feed storage tank 70 includes, as its major component, cyclohexanol, and may also include residual amounts of cyclohexanone. For simplicity, the resultant product 190 is the liquid cyclohexanol, which exits the feed storage tank 70 as fluid stream 21 as described in Step 1005 above and Step 1010 subsequently.

In Step 1010, the liquid cyclohexanol 21 is vaporized within the first cyclohexanol dehydrogenation reactor 22A to form vaporized cyclohexanol.

In Step 1010, this may be done by heating the interior region 33 of the first dehydrogenation reactor 22A such that the temperature of the fluid stream 21 is above the vaporization temperature of the components of the fluid stream 21 (i.e., above the vaporization temperature of the cyclohexanol and cyclohexanone and any other residual hydrocarbon components of the fluid stream 21). In certain embodiments of the method, the interior region 33 is heated to a temperature from 325 to 395° C. at a pressure ranging from 138 to 210 kPa, such as 360° C. at 172 kPa. In one embodiment of the method for heating the interior region 33, as shown in FIG. 2, a heated combustion gas 31 is introduced through the hollow tube 37, wherein heat radiates (flows) from the gas 31 through the tube 37 to heat the interior region 33 of the first dehydrogenation reactor 22A.

Next, in Step 1020, the vaporized cyclohexanol is dehydrogenated in the presence of a dehydrogenation catalyst to form vaporized cyclohexanone and hydrogen gas. Step 1020 may be accomplished contacting the vaporized cyclohexanol with the dehydrogenation catalyst 36, which promotes the dehydrogenation of the vaporized cyclohexanol to vaporized cyclohexanone and hydrogen gas.

Next, in Step 1030, the vaporized cyclohexanone and remaining vaporized cyclohexanol are condensed within the first condenser 24 to form liquid cyclohexanone and liquid cyclohexanol.

In certain embodiments of the method of Step 1030, the formed vaporized cyclohexanone and remaining vaporized cyclohexanol and hydrogen gas may be transferred from the first cyclohexanol dehydrogenation reactor 22A to a first condenser 24. As shown in FIG. 1, this is done by removing the vaporized cyclohexanone and remaining vaporized cyclohexanol and hydrogen gas through the outlet 32 of the first dehydrogenation reactor 22A and introducing the vaporized cyclohexanone and remaining vaporized cyclohexanol and hydrogen gas through the inlet 42 of the condenser 24 as a fluid stream 43. Next, the fluid stream 43 of vaporized cyclohexanone and remaining vaporized cyclohexanol is cooled within the condenser 24 to reduce the temperature of the vapor below the condensation temperature of both cyclohexanone and cyclohexanol, such as from 120 to 170° C., such as 140° C.

In certain embodiments of the method as in Step 1030, wherein the condenser 24 is as described above and illustrated in FIG. 3, a cooling fluid 47 is introduced through hollow tubes 46 contained within the interior region 48 of the condenser 24 that contacts the fluid stream 43 and cools the fluid stream 43 to condense the vaporized cyclohexanone and remaining vaporized cyclohexanol to liquid cyclohexanone and liquid cyclohexanol.

Next, in Step 1040, the hydrogen gas is removed.

In certain embodiments, the removal of hydrogen gas in Step 1040 occurs after Step 1030, while in alternative methods the removal of hydrogen gas in Step 1040 occurs simultaneously with Step 1030.

In certain embodiments, such as wherein the condenser 24 is as illustrated in FIG. 3 is utilized in the method, Step 1040 proceeds wherein the hydrogen gas is removed from the first condenser 24 through a vent 59 after Step 1030 wherein the liquid cyclohexanone and liquid cyclohexanol are formed.

Next, in Step 1050, the liquid cyclohexanone and liquid cyclohexanol are vaporized within the second dehydrogenation reactor 22. In certain embodiments, the formed liquid cyclohexanone and remaining liquid cyclohexanol within the second cyclohexanol dehydrogenation reactor are heated to a temperature greater than the temperature for the step of vaporizing the liquid cyclohexanol within the first cyclohexanol dehydrogenation reactor in Step 1010 above.

In certain embodiments, such as shown in FIG. 1, Step 1050 proceeds wherein the liquid cyclohexanone and cyclohexanol are removed from the first condenser 24 through the outlet 44 as a fluid stream 45 and is introduced through the inlet 30 of the next adjacent cyclohexanol dehydrogenation reactor 22 (i.e., the second dehydrogenation reactor 22 as provided in FIG. 1).

Within the next adjacent cyclohexanol dehydrogenation reactor 22, the fluid stream 45 is vaporized by heating the interior region 33 of the second dehydrogenation reactor 22B such that the temperature of the fluid stream 45 is above the vaporization temperature of the components of the fluid stream 45 (i.e., above the vaporization temperature of the cyclohexanol and cyclohexanone and any other residual hydrocarbon components in the fluid stream 45). In certain embodiments, the interior region 33 is heated to a temperature from 325 to 395° C. at a pressure ranging from 138 to 210 kPa, such as 360° C. at 172 kPa.

In one embodiment for heating the interior region 33, as shown in FIG. 2, a heated combustion gas 31 is introduced through the hollow tube 37 of the second dehydrogenation reactor 22B, wherein heat radiates (flows) from the gas 31 through the tube 37 to heat the interior region 33.

Next, in Step 1060, the vaporized cyclohexanol is dehydrogenated in the presence of a dehydrogenation catalyst in the second cyclohexanol dehydrogenation reactor to form additional vaporized cyclohexanone (separate from the vaporized cyclohexanone formed in Step 1030 above and also present within the second cyclohexanol dehydrogenation reactor in Steps 1050 and 1060) and additional hydrogen gas separate from the hydrogen gas formed in Step 1030 above).

In certain embodiments, such as in the embodiment as illustrated in FIG. 2, Step 1060 proceeds by contacting the vaporized cyclohexanol with the dehydrogenation catalyst 36 within the second dehydrogenation reactor 22, which promotes the dehydrogenation of the vaporized cyclohexanol to vaporized cyclohexanone and hydrogen gas.

Next, in Step 1070, the vaporized cyclohexanone (formed either in Step 1030 or Step 1060) and any residual vaporized cyclohexanol are condensed within a second condenser 25 to form a product.

In certain embodiments, such as in the embodiment as illustrated in FIG. 1, Step 1070 proceeds wherein the formed vaporized cyclohexanone (formed either in Step 1030 or Step 1060) and remaining vaporized cyclohexanol and hydrogen gas are transferred from the last cyclohexanol dehydrogenation reactor 22B to a second condenser 25 (the last condenser 25 as shown in FIG. 1). The second condenser 25 is typically of the same design as the first condenser 24, as described above in FIG. 3. In this embodiment, the vaporized cyclohexanone and remaining vaporized cyclohexanol and hydrogen gas are removed through the outlet 32 of the second dehydrogenation reactor 22 and introduced through the inlet 42 of the second condenser 25 as a fluid stream 47.

The fluid stream 47 of vaporized cyclohexanone and remaining vaporized cyclohexanol is then condensed to liquid form within the second condenser 25. This is done by cooling the fluid stream 47 of vaporized cyclohexanone and remaining vaporized cyclohexanol to reduce the temperature of the vapor below the condensation temperature of both cyclohexanone and cyclohexanol, such as cooling to a temperature ranging from 140 to 180° C., such as 160° C.

In certain embodiments of the present method, the concentration of liquid cyclohexanone in the product formed in Step 1070, produced according to the present invention while operating two dehydrogenation reactors 22A, 22B and two condensers 24, 25 in series as described in FIG. 1 above, is present in an amount from 85 to 90 weight percent based upon the total weight of the product, with residual unreacted cyclohexanol present in an amount of 3 to 8 weight percent.

Next, in Step 1080, the hydrogen gas is removed.

In certain embodiments of the method, the hydrogen gas is removed after Step 1070. In alternative embodiments of the method, the hydrogen gas is removed as Step 1070 is proceeding.

In certain embodiments, such as in the unit as illustrated as in FIG. 3, Step 1080 proceeds wherein the hydrogen gas is removed from the second condenser 25 through a vent 59 after the condensation of the vaporized cyclohexanone (formed either in Step 1030 or Step 1060) and remaining vaporized cyclohexanol.

Next, in Step 1090, the formed cyclohexanone is separated from the cyclohexanol in the product.

In certain embodiments of the method, such as shown in FIG. 1, Step 1090 proceeds wherein the formed liquid cyclohexanone and remaining liquid cyclohexanol are removed from the second condenser 24 as a fluid stream 53 and introduced through the inlet 60 and into the first of the series of distillation units 26. Next, the liquid cyclohexanone is separated from any residual liquid cyclohexanol or other hydrocarbon products in the product within the first distillation unit 26. This is done by slowly heating the fluid stream 53 within the interior region 65 in FIG. 4 of the first distillation unit 26 to a temperature sufficient to volatize stepwise each component of the fluid stream 53. The separated components are removed stepwise from the first distillation unit 26 through the vapor outlet 61 as shown in FIG. 1 and stored in separate containers, one of which (container 63) contains high purity cyclohexanone as a product 51.

The product 51 may alternatively be introduced to one or more additional distillation units to further separate the cyclohexanone from any residual cyclohexanol or other hydrocarbon products in a manner similar to that provided in the first distillation unit.

The present invention thus provides a method for efficiently forming high purity cyclohexanone from cyclohexanol that takes advantage of Le Châtelier's principle that utilizes dehydrogenation reactors and condensers coupled in series that allows the removal of hydrogen gas between each successive dehydrogenation step, thus driving the reaction towards the formation of additional cyclohexanone prior to the need for distillation. By reducing the concentration of unreacted cyclohexanol in the resultant product in accordance with the method of the present invention, as compared with tradition methods where a single cyclohexanol dehydrogenation reactor coupled to a distillation unit is utilized, the amount of cyclohexanol that needs to be removed from this product during a subsequent distillation process and recycled (i.e., reintroduced to the single dehydrogenation reactor after recovery from distillation) is correspondingly reduced.

The following examples are intended to illustrate the invention and are not to be viewed in any way as limiting to the scope of the invention.

EXAMPLES

Experiment 1:

Dehydrogenation reactors (A) and (B) were operated in series as shown generally in FIG. 1 above to determine the effect on the cyclohexanol, cyclohexanone, and residual dimer concentrations discharging from the final reactor. The setup of the reactors had (A) as the first reactor and (B) as the second reactor. The variables manipulated were the flow rate of the reactants entering the second reactor (B), the discharge temperature of dehydrogenation reactor (B) and the discharge temperature of the dehydrogenation reactor (A).

The discharge temperature of dehydrogenation reactor (A) was adjusted in order to change the concentration of cyclohexanone in the feed to the second dehydrogenation reactor, (B). A total of 10 test runs were conducted.

Tables 1, 2 and 3 illustrate the effect of cyclohexanone concentration (Table 1), cyclohexanol concentration (Table), and residual dimer concentration within these ten runs.

As provided in Table 1, the concentration of cyclohexanone entering the first dehydrogenation reactor (A) ranged between 4 and 6 weight percent, while the concentration of cyclohexanol entering the first dehydrogenation reactor ranged from 89 to 91 weight percent.

TABLE 1

| Run # | Flow Rate of Reactants Entering Reactor (B) (kg/hr) | Discharge Temperature Exiting Reactor (B) (° C.) | Cyclohexanone Feed Concentration entering Reactor (B) (%) | Cyclohexanone Discharge Concentration from Reactor (B) (%) |
|---|---|---|---|---|
| 1 | 2734 | 395.2 | 54.24 | 90.31 |
| 2 | 3329 | 395.0 | 44.49 | 89.32 |
| 3 | 4022 | 383.2 | 40.97 | 82.55 |
| 4 | 3971 | 384.1 | 35.43 | 83.95 |
| 5 | 3013 | 395.3 | 46.25 | 89.49 |
| 6 | 2967 | 395.1 | 50.52 | 90.22 |
| 7 | 2664 | 395.4 | 55.20 | 90.54 |
| 8 | 3522 | 389.9 | 53.77 | 85.02 |
| 9 | 3500 | 392.4 | 53.93 | 86.29 |
| 10 | 3505 | 397.8 | 54.37 | 87.67 |

TABLE 2

| Run # | Flow Rate of Reactants Entering Reactor (B) (kg/hr) | Discharge Temperature Exiting Reactor (B) (° C.) | Cyclohexanol Feed Concentration entering Reactor (B) (%) | Cyclohexanol Discharge Concentration from Reactor (B) (%) |
|---|---|---|---|---|
| 1 | 2734 | 395.2 | 41.29 | 3.54 |
| 2 | 3329 | 395.0 | 50.52 | 4.73 |
| 3 | 4022 | 383.2 | 54.40 | 11.94 |
| 4 | 3971 | 384.1 | 60.04 | 10.04 |
| 5 | 3013 | 395.3 | 48.47 | 3.53 |
| 6 | 2967 | 395.1 | 44.9 | 3.43 |
| 7 | 2664 | 395.4 | 40.23 | 2.81 |
| 8 | 3522 | 389.9 | 40.73 | 8.33 |
| 9 | 3500 | 392.4 | 40.84 | 7.20 |
| 10 | 3505 | 397.8 | 40.59 | 5.75 |

TABLE 3

| Run # | Flow Rate of Reactants Entering Reactor (B) (lb/hr) | Discharge Temperature Exiting Reactor (B) (° C.) | Dimer Feed Concentration entering Reactor (B) (%) | Dimer Discharge Concentration from Reactor (B) (%) | % Increase in Dimer Concentration formed in Reactor (B) |
|---|---|---|---|---|---|
| 1 | 2734 | 395.2 | 4.49 | 5.82 | 1.33 |
| 2 | 3329 | 395.0 | 4.39 | 5.65 | 1.26 |
| 3 | 4022 | 383.2 | 4.51 | 5.27 | 0.76 |
| 4 | 3971 | 384.1 | 4.57 | 5.39 | 0.82 |
| 5 | 3013 | 395.3 | 5.15 | 6.64 | 1.49 |
| 6 | 2967 | 395.1 | 4.46 | 6.08 | 1.62 |
| 7 | 2664 | 395.4 | 4.43 | 6.29 | 1.86 |
| 8 | 3522 | 389.9 | 5.42 | 6.41 | 0.99 |
| 9 | 3500 | 392.4 | 5.15 | 6.25 | 1.10 |
| 10 | 3505 | 397.8 | 4.98 | 6.29 | 1.31 |

The concentration of cyclohexanone and cyclohexanol leaving the second series reactor (B) in Tables 1-3, respectively, above were mathematically determined according to the following Equations 1-2, while the percentage change in dimer concentration leaving reactor (B) was calculated according to Equation 3 below:

Cyclohexanone Final Concentration=[−20.8−
0.001946*(Flow Rate of Reactants into(*B*))+
0.3294* (Discharge Temperature from(*B*))−
0.1360*(Cyclohexanone Feed Concentration
to(*B*))]                                                                              Equation 1:

Cyclohexanol Final Conc.=[140.0+0.001928*(Flow Rate of Reactants into(B))−0.3639* (Discharge Temperature from(B))−0.1127*(Cyclohexanol Feed Concentration to(B)]   Equation 2:

Dimer Concentration Change(%)=[−4.33−0.000232* (Flow Rate of Reactants into(B))+0.018* (Discharge Temperature from (B))   Equation 3:

As Tables 1-3 confirm, a large majority of the cyclohexanol entering the second reactor (B) was transformed into cyclohexanone via dehydrogenation, with a slight increase in the corresponding amount of dimer concentration.

It is to be understood that the appended claims are not limited to express and particular compounds, surface treatment materials, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims, The invention has been described in an illustrative manner, and it is to be understood that the terminology which has been used is intended to be in the nature of words of description rather than of limitation. Obviously, many modifications and variations of the present invention are possible in light of the above teachings. The invention may be practiced otherwise than as specifically described.

What is claimed is:

1. A method for forming cyclohexanone from cyclohexanol, the method comprising:
   introducing liquid cyclohexanol into a first cyclohexanol dehydrogenation reactor;
   vaporizing the liquid cyclohexanol within the first cyclohexanol dehydrogenation reactor to form vaporized cyclohexanol;
   dehydrogenating the vaporized cyclohexanol in the presence of a dehydrogenation catalyst to form vaporized cyclohexanone and hydrogen gas;
   condensing the formed vaporized cyclohexanone and any remaining vaporized cyclohexanol within a first condenser to form liquid cyclohexanone and liquid cyclohexanol;
   removing the formed hydrogen gas;
   vaporizing the formed liquid cyclohexanone and liquid cyclohexanol within a second cyclohexanol dehydrogenation reactor to form vaporized cyclohexanone and vaporized cyclohexanol;
   dehydrogenating the vaporized cyclohexanol from the second cyclohexanol dehydrogenation reactor in the presence of a dehydrogenation catalyst to form additional vaporized cyclohexanone and additional hydrogen gas; and
   condensing the formed vaporized cyclohexanone and formed additional vaporized cyclohexanone and any remaining vaporized cyclohexanol within a second condenser to form liquid cyclohexanone and liquid cyclohexanol as a product.

2. The method according to claim 1, further comprising:
   separating the liquid cyclohexanone from the liquid cyclohexanol of the product within a first distillation unit.

3. The method according to claim 2, further comprising: removing the formed additional hydrogen gas.

4. The method according to claim 1, wherein the step of vaporizing the liquid cyclohexanol within the first cyclohexanol dehydrogenation reactor comprises heating the liquid cyclohexanol within the first cyclohexanol dehydrogenation reactor to a temperature from 325 degrees Celsius to 395 degrees Celsius at a pressure ranging from 138 to 210 kilopascals.

5. The method according to claim 1, wherein the step of dehydrogenating the vaporized cyclohexanol in the presence of a dehydrogenation catalyst to form vaporized cyclohexanone and hydrogen gas comprises:
   contacting the vaporized cyclohexanol with a first catalyst bed within the first cyclohexanol dehydrogenation reactor, the first catalyst bed comprising a zinc catalyst on a first calcium oxide carrier.

6. The method according to claim 1, wherein the step of condensing the formed vaporized cyclohexanone and any remaining vaporized cyclohexanol within a first condenser to form liquid cyclohexanone and liquid cyclohexanol comprises:
   cooling the formed vaporized cyclohexanone and formed vaporized cyclohexanol within the condenser to a first temperature below the condensation temperature of cyclohexanol and below the condensation temperature of cyclohexanone.

7. The method according to claim 1, wherein the step of removing the formed hydrogen gas occurs after the step of condensing the formed vaporized cyclohexanone and any remaining vaporized cyclohexanol within a first condenser to form liquid cyclohexanone and liquid cyclohexanol and occurs before the step of vaporizing the formed liquid cyclohexanone and liquid cyclohexanol within a second cyclohexanol dehydrogenation reactor to form vaporized cyclohexanone and vaporized cyclohexanol.

8. The method according to claim 1, wherein the step of removing the formed hydrogen gas occurs simultaneously with the step of condensing the formed vaporized cyclohexanone and any remaining vaporized cyclohexanol within a first condenser to form liquid cyclohexanone and liquid cyclohexanol and occurs before the step of vaporizing the formed liquid cyclohexanone and liquid cyclohexanol within a second cyclohexanol dehydrogenation reactor to form vaporized cyclohexanone and vaporized cyclohexanol.

9. The method according to claim 1, wherein the step of vaporizing the formed liquid cyclohexanone and liquid cyclohexanol within a second cyclohexanol dehydrogenation reactor to form vaporized cyclohexanone and vaporized cyclohexanol comprises:
heating the formed liquid cyclohexanone and remaining liquid cyclohexanol within the second cyclohexanol dehydrogenation reactor to a temperature greater than the temperature for the step of vaporizing the liquid cyclohexanol within the first cyclohexanol dehydrogenation reactor.

10. The method according to claim 9, wherein the temperature is from 325 degrees Celsius to 395 degrees Celsius at a pressure ranging from 138 to 210 kilopascals.

11. The method according to claim 1, wherein the step of dehydrogenating the vaporized cyclohexanol from the second cyclohexanol dehydrogenation reactor in the presence of a dehydrogenation catalyst to form additional vaporized cyclohexanone and additional hydrogen gas comprises:
contacting the vaporized cyclohexanol with a second catalyst bed within the second cyclohexanol dehydrogenation reactor, the second catalyst bed comprising the additional amount zinc catalyst on a second calcium oxide carrier.

12. The method according to claim 1, wherein the product comprises from 85 to 90 weight percent of cyclohexanone based on the total weight of the product.

13. The method according to claim 1, wherein the product comprises from 3 to 8 weight percent of cyclohexanol based on the total weight of the product.

14. The method according to claim 1, further comprising:
vaporizing the product within a third cyclohexanol dehydrogenation reactor to form vaporized cyclohexanone and vaporized cyclohexanol;
dehydrogenating the vaporized cyclohexanol from the product in the presence of a dehydrogenation catalyst to form a vaporized cyclohexanone and hydrogen gas; and
condensing the formed vaporized cyclohexanone and formed additional vaporized cyclohexanone from the product and any remaining vaporized cyclohexanol from the product to form liquid cyclohexanone and liquid cyclohexanol within a third condenser to form a second product.

15. The method according to claim 14, further comprising:
(r) separating the liquid cyclohexanone from the liquid cyclohexanol of the second product within a third distillation unit.

16. A method for forming cyclohexanone from cyclohexane, the method comprising:
forming liquid cyclohexanol from cyclohexane;
introducing liquid cyclohexanol into a first cyclohexanol dehydrogenation reactor;
vaporizing the liquid cyclohexanol within the first cyclohexanol dehydrogenation reactor to form vaporized cyclohexanol;
dehydrogenating the vaporized cyclohexanol in the presence of a dehydrogenation catalyst to form vaporized cyclohexanone and hydrogen gas;
condensing the formed vaporized cyclohexanone and any remaining vaporized cyclohexanol within a first condenser to form liquid cyclohexanone and liquid cyclohexanol;
removing the formed hydrogen gas;
vaporizing the formed liquid cyclohexanone and liquid cyclohexanol within a second cyclohexanol dehydrogenation reactor to form vaporized cyclohexanone and vaporized cyclohexanol; dehydrogenating the vaporized cyclohexanol from the second cyclohexanol dehydrogenation reactor in the presence of a dehydrogenation catalyst to form additional vaporized cyclohexanone and additional hydrogen gas; and
condensing the formed vaporized cyclohexanone and formed additional vaporized cyclohexanone and any remaining vaporized cyclohexanol within a second condenser to form liquid cyclohexanone and liquid cyclohexanol as a product.

17. The method according to claim 16, wherein the step of forming liquid cyclohexanol from cyclohexane comprises catalytically oxidizing cyclohexane in the presence of air and a cobalt catalyst within a reactor to form cyclohexanol.

18. The method according to claim 17, wherein the step of forming liquid cyclohexanol from cyclohexane further comprises separating the formed cyclohexanol from the cobalt catalyst and any remaining cyclohexane within a second distillation unit prior to the step of introducing liquid cyclohexanol into the first cyclohexanol dehydrogenation reactor.

* * * * *